US012702759B2

(12) United States Patent
Zhang

(10) Patent No.: US 12,702,759 B2
(45) Date of Patent: Aug. 11, 2026

(54) DISPOSABLE INJECTION NEEDLE

(71) Applicant: Tianjin Huahong Technology Co., Ltd., Tianjin (CN)

(72) Inventor: Libo Zhang, Tianjin (CN)

(73) Assignee: TIANJIN HUAHONG TECHNOLOGY CO., LTD., Tianjin (CN)

( * ) Notice: Subject to any disclaimer, the term of this patent is extended or adjusted under 35 U.S.C. 154(b) by 507 days.

(21) Appl. No.: 18/135,401

(22) Filed: Apr. 17, 2023

(65) Prior Publication Data

US 2023/0330340 A1 Oct. 19, 2023

(30) Foreign Application Priority Data

Apr. 18, 2022 (CN) ........................ 202210405420.2

(51) Int. Cl.
*A61M 5/20* (2006.01)
*A61M 5/32* (2006.01)

(52) U.S. Cl.
CPC ........ *A61M 5/2033* (2013.01); *A61M 5/3271* (2013.01); *A61M 5/3272* (2013.01);
(Continued)

(58) Field of Classification Search
CPC .............. A61M 5/3272; A61M 5/3271; A61M 5/2033; A61M 2005/3267;
(Continued)

(56) References Cited

U.S. PATENT DOCUMENTS 8,016,797 B2 * 9/2011 Gratwohl .............. A61M 5/326 604/171
12,064,608 B2 * 8/2024 Shi ...................... A61M 5/3213
(Continued)

FOREIGN PATENT DOCUMENTS

CN 108992744 A 12/2018
CN 111214729 A 6/2020
(Continued)

OTHER PUBLICATIONS

Clarivate English translation of WO2021168781A1 by Lu published Sep. 2, 2021 (Year: 2021).*
(Continued)

*Primary Examiner* — Stephanie Sebasco Cheng
(74) *Attorney, Agent, or Firm* — Scully, Scott, Murphy & Presser, P.C.

(57) ABSTRACT

A disposable injection needle is provided. The disposable injection needle includes a needle holder, a housing, a sleeve, a core, and a spring. A first end of the housing is connected to a second end of the needle holder, a second end of the housing has a housing opening. A first end of the sleeve is located in the housing, a second end of the sleeve has a sleeve opening and protrudes from the housing opening. A first end of the core is disposed in the housing and sleeved outside the needle holder, and a second end of the core includes a core hole through which the first end of the tube needle extends. The spring provides an elastic force to axially move the sleeve toward outside of the housing. The sleeve retracts into the housing under an external force, to expose the tube needle through the sleeve opening.

20 Claims, 6 Drawing Sheets

(52) U.S. Cl.
CPC ................. *A61M 2005/208* (2013.01); *A61M 2005/3247* (2013.01); *A61M 2005/3254* (2013.01); *A61M 2005/3267* (2013.01)

(58) Field of Classification Search
CPC .. A61M 2005/3247; A61M 2005/3254; A61M 2005/208
See application file for complete search history.

(56) References Cited

U.S. PATENT DOCUMENTS

| | | | |
|---|---|---|---|
| 2009/0259178 | A1 | 10/2009 | Brechbuehler et al. |
| 2009/0259196 | A1 | 10/2009 | Gratwohl |
| 2021/0138159 | A1 | 5/2021 | Shi et al. |

FOREIGN PATENT DOCUMENTS

| | | | |
|---|---|---|---|
| CN | 113476044 | A | 10/2021 |
| EP | 3574946 | A1 | 12/2019 |
| EP | 3875027 | A1 | 9/2021 |
| WO | 2021168781 | A1 | 9/2021 |

OTHER PUBLICATIONS

Extended European Search Report dated Aug. 24, 2023 received in European Patent Application No. EP 23168246.9.
Chinese Office Action dated Jan. 25, 2026 received in Chinese Application No. 202210405420.2.

* cited by examiner

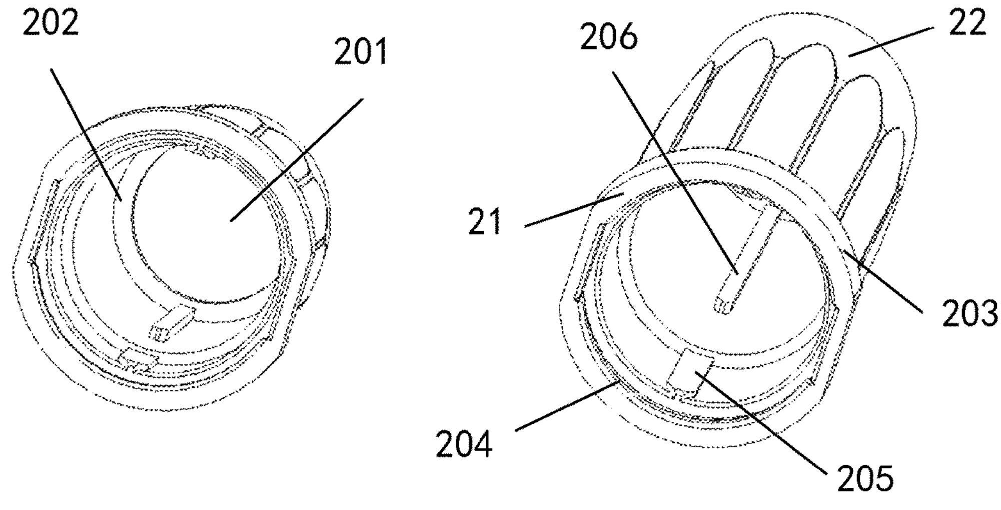
FIG. 3
FIG. 4
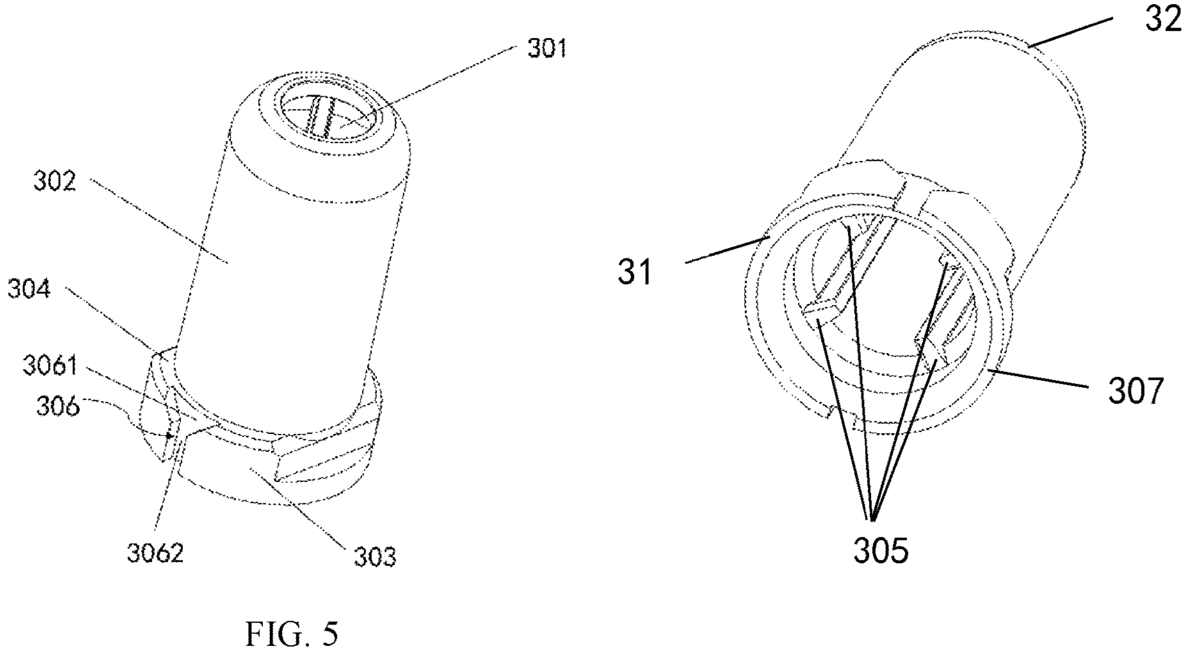
FIG. 5
FIG. 6

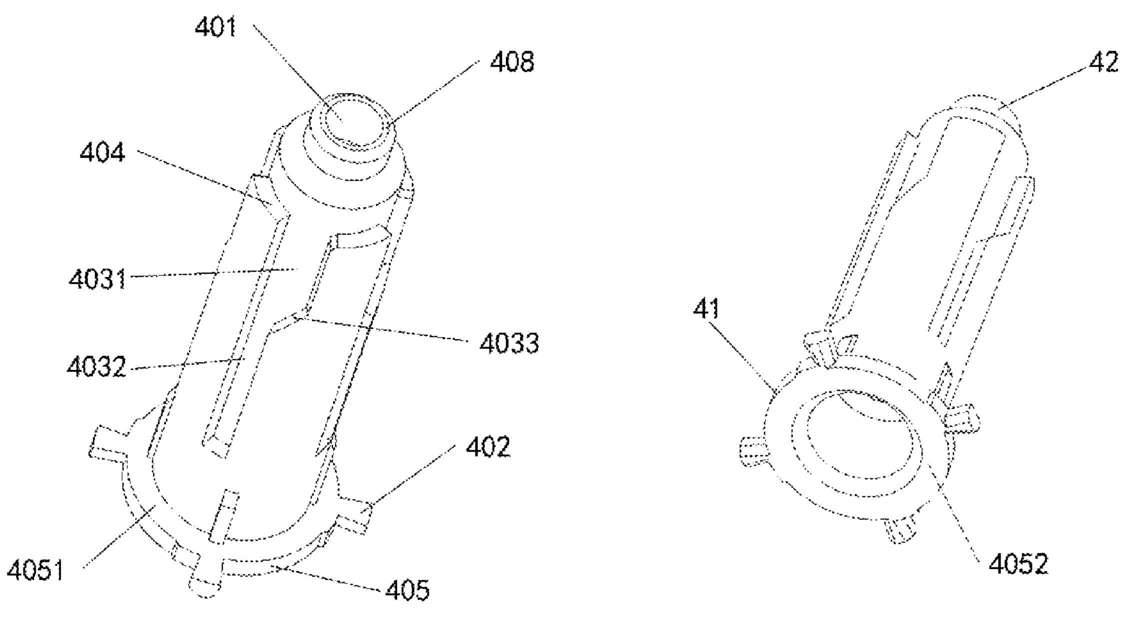
FIG. 7
FIG. 8
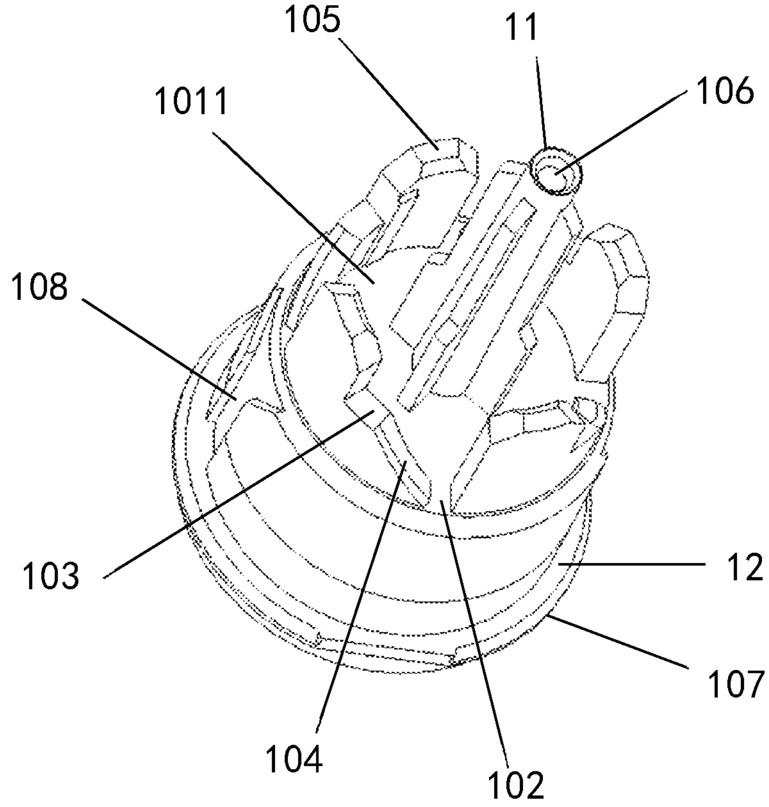
FIG. 9

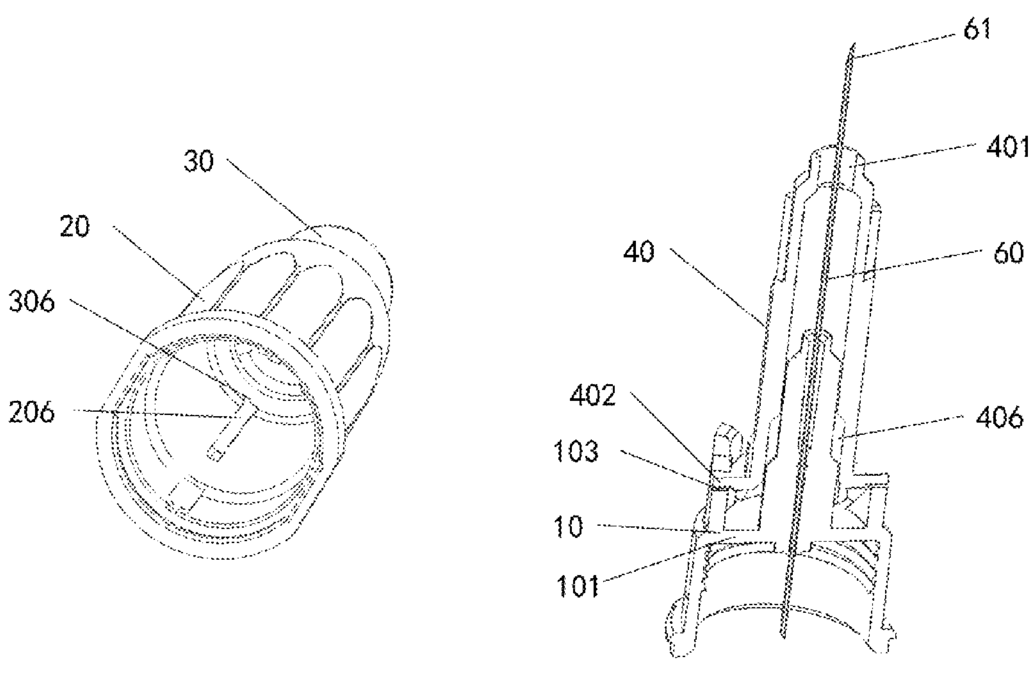
FIG. 10
FIG. 11
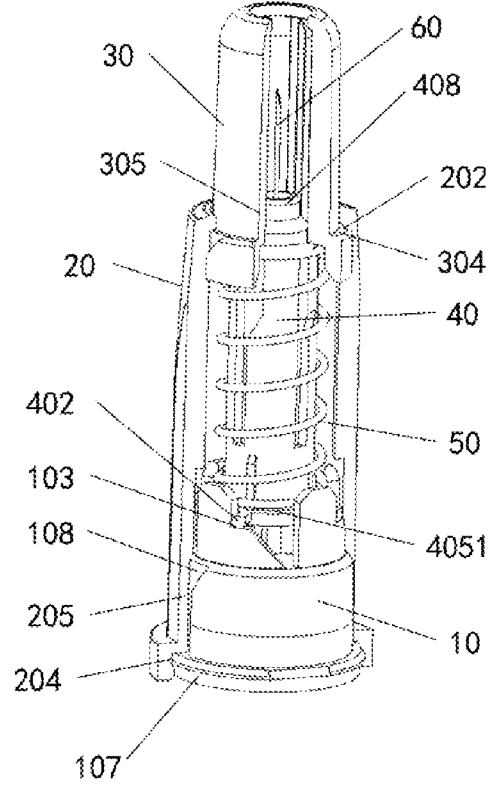
FIG. 12

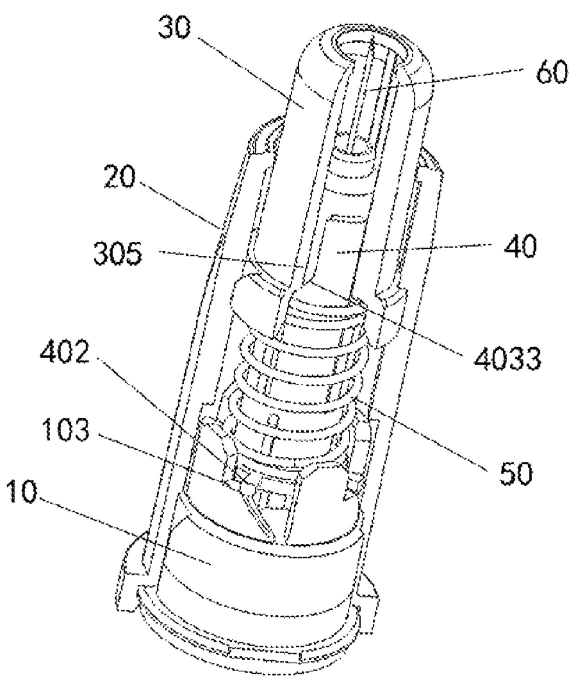
FIG. 13
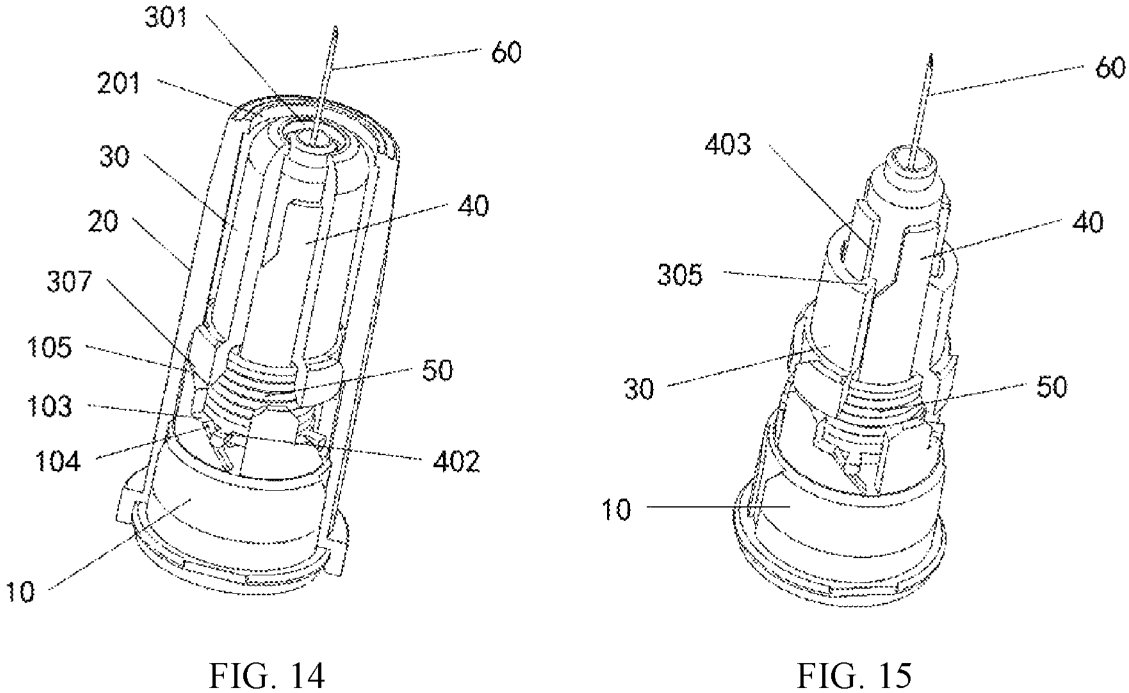
FIG. 14
FIG. 15

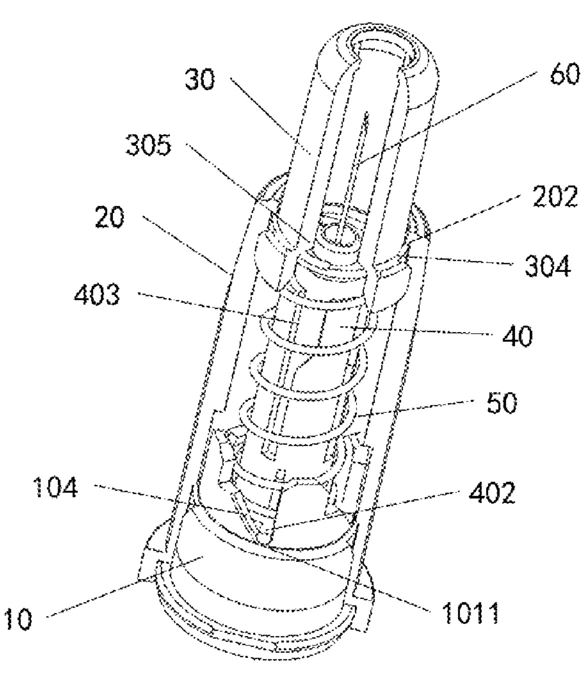
FIG. 16
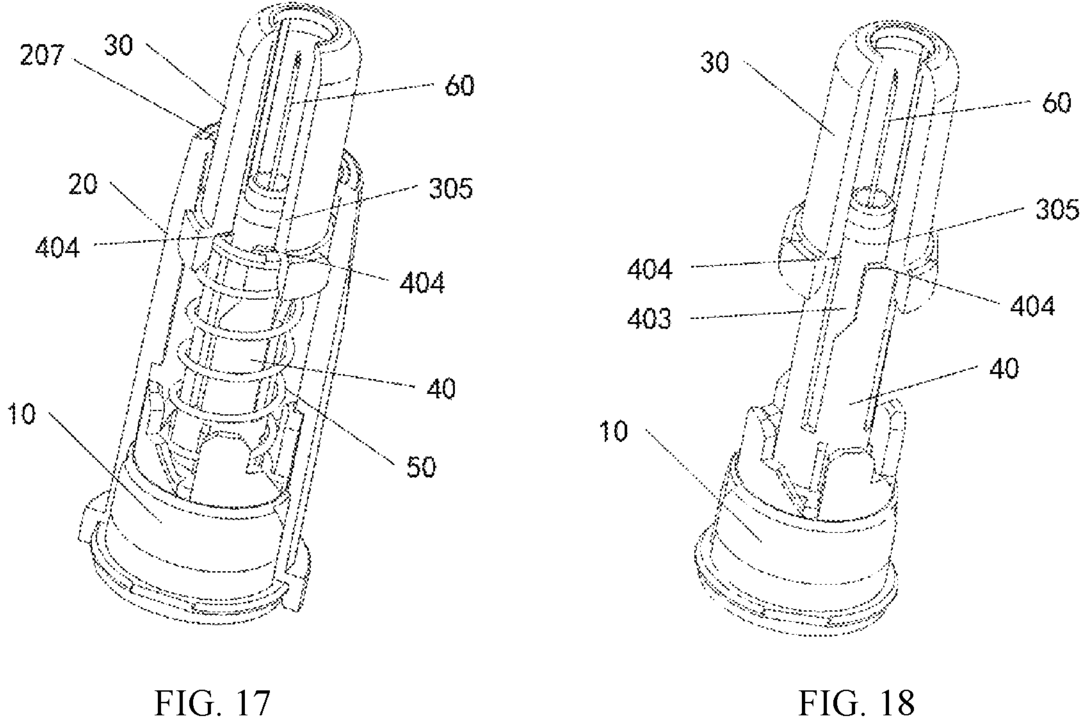
FIG. 17
FIG. 18

DISPOSABLE INJECTION NEEDLE

CROSS-REFERENCE TO RELATED APPLICATION

The present application claims priority to Chinese Patent Application No. 202210405420.2, filed on Apr. 18, 2022, the content of which is incorporated herein by reference in its entirety.

TECHNICAL FIELD

The present disclosure relates to the field of medical instruments, and in particular, to a disposable injection needle.

BACKGROUND

Insulin injection needles have been widely used as a tool for treating diabetes. The main function of the insulin injection needles is to inject insulin into diabetic patients to control the blood glucose of the patients.

The common injection needle currently on the market that are used with an insulin injection pen consists of a large sleeve, a small sleeve, a needle holder, a tube needle, and dialysis paper. After the large sleeve and the small sleeve are removed, the needle tip of the tube needle is always exposed to the outside, which can increase the infection probability to patients who use it again. Further, the used needle can cause cross infection by accidentally injuring others.

SUMMARY

The present disclosure provides a disposable injection needle, which has a protection function at an patient-end, thereby avoiding infection caused by needle tip injury and repeated use and being convenient and quick to use.

According to an embodiment of the present disclosure, a disposable injection needle is provided, and includes a needle holder, a housing, a sleeve, a core and a spring. The needle holder has a first end and a second end, and a tube needle is provided to the needle holder and passes through the needle holder. The housing has a first end and a second end, the first end of the housing is connected to the second end of the needle holder, and the second end of the housing has a housing opening. The sleeve has a first end and a second end, the first end of the sleeve is located in the housing, and the second end of the sleeve has a sleeve opening and protrudes from the housing opening. A part of the sleeve is axially slidable inside the housing. The core has a first end and a second end, the first end of the core is disposed in the housing and sleeved outside the needle holder, and the second end of the core includes a core hole through which the first end of the tube needle extends. The spring is configured to provide an elastic force to axially move the sleeve toward outside of the housing. The sleeve is configured to retract into the housing under an external force, to expose the tube needle through the sleeve opening. The first end of the core is provided with a core guiding portion extending radially, the needle holder is provided with a guiding engagement portion, and the core guiding portion engages with the guiding engagement portion at an assembled position of the core and the needle holder. The core guiding portion is configured to move along the guiding engagement portion with movement of the sleeve toward interior of the housing, to guide the core to rotate in a circumferential direction of the disposable injection needle, and the core guiding portion is configured to move to disengage from the guiding engagement portion.

BRIEF DESCRIPTION OF DRAWINGS

These and other aspects and features of the present disclosure will be apparent from the following description of embodiments in conjunction with the accompanying drawings.

FIG. 3 and FIG. 4 are perspective views of a housing according to an embodiment of the present disclosure, which are observed respectively from different viewing angles.

FIG. 5 and FIG. 6 are perspective views of a sleeve according to an embodiment of the present disclosure, which are observed respectively from different viewing angles.

FIG. 7 and FIG. 8 are perspective views of a core according to an embodiment of the present disclosure, which are observed respectively from different viewing angles.

FIG. 9 is a perspective structural view of a needle holder according to an embodiment of the present disclosure.

FIG. 10 is an assembly schematic view of a housing and a sleeve according to an embodiment of the present disclosure.

FIG. 11 is an assembly sectional view of a core and a needle holder according to an embodiment of the present disclosure.

FIG. 12 is a schematic structural view of a disposable injection needle in an initial assembly state according to an embodiment of the present disclosure, in which a portion of a housing and a portion of a sleeve are removed.

FIG. 13 is a schematic structural view of a disposable injection needle in use according to an embodiment of the present disclosure, in which a portion of a housing and a portion of a sleeve are removed.

FIG. 14 is a schematic structural view of a disposable injection needle in use according to an embodiment of the present disclosure, in which a tube needle is in a longest exposed state and a portion of the disposable injection needle is removed to display an internal structure.

FIG. 15 is a schematic structural view of a disposable injection needle in use according to an embodiment of the present disclosure, in which a tube needle is in a longest exposed state with a housing removed.

FIG. 16 is a schematic structural view of a disposable injection needle according to an embodiment of the present disclosure after use.

FIG. 17 is a schematic structural view of a disposable injection needle according to an embodiment of the present disclosure that is subjected to a downward external force again after use, in which a portion of the disposable injection needle is removed to display an internal structure.

FIG. 18 is a schematic structural view of the disposable injection needle shown in FIG. 17 with the housing and the spring removed.

DESCRIPTION OF EMBODIMENTS

Figure 1:
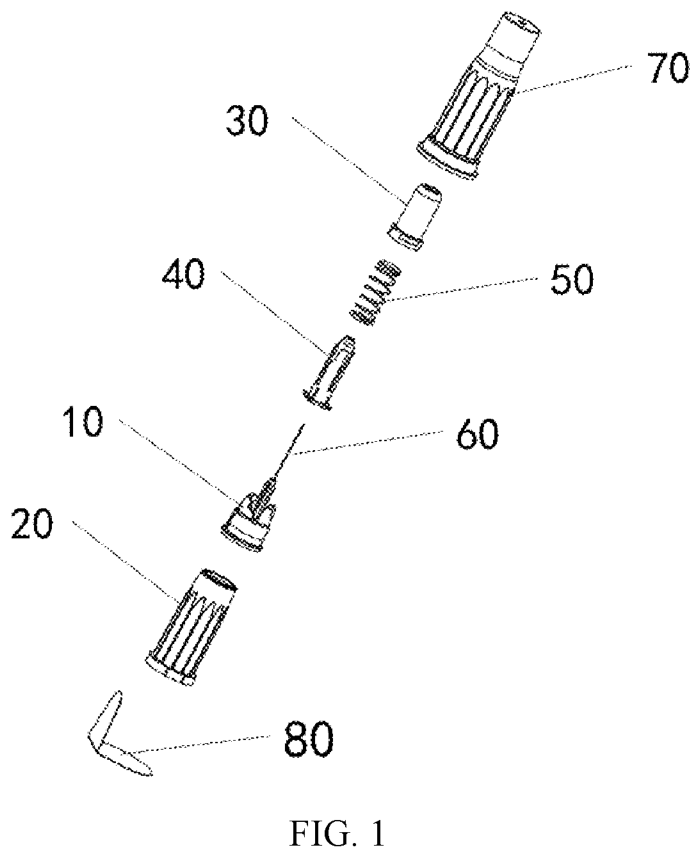
FIG. 1 is a perspective view of a disposable injection needle according to an embodiment of the present disclosure.

The technical solutions of the present disclosure will be further described in detail below through embodiments in combination with the accompanying drawings. In the description, the same or similar reference signs indicate the same or similar components. The following description of the embodiments of the present disclosure with reference to the accompanying drawings is intended to explain the general inventive concept of the present disclosure, and should not be construed as limitation to the present disclosure.

A disposable injection needle according to an embodiment of the present disclosure is described in detail with reference to the accompanying drawings, and it should be noted that some features or components are not specifically shown in the drawings for the clarity of illustration.

Figure 2:
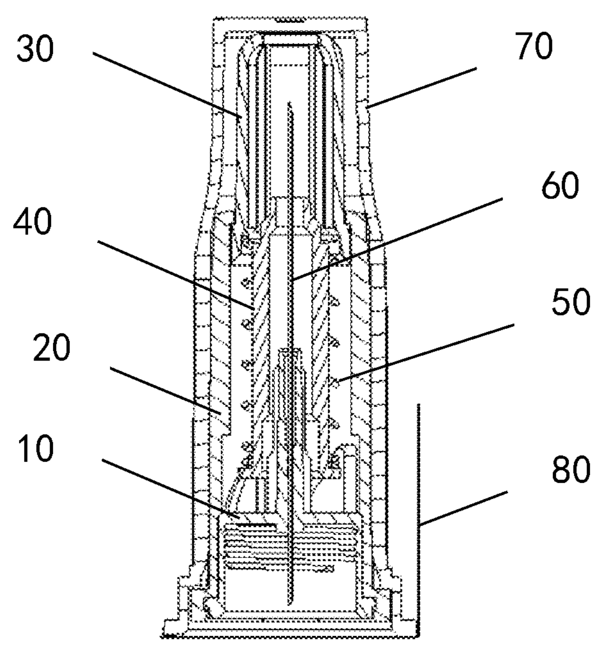
FIG. 2 is a schematic sectional view of the disposable injection needle shown in FIG. 1.

Referring to FIG. 1, a disposable injection needle according to an embodiment of the present disclosure includes a needle holder 10, a housing 20, a sleeve 30, a core 40, and a spring 50. The needle holder 10 is provided with a tube needle 60, which passes through the needle holder 10. The needle holder has a first end 11 and a second end 12, as shown in FIG. 9. As shown in FIGS. 2 to 4, a first end 21 of the housing 20 is connected to the second end 12 of the needle holder 10, and a second end 22 of the housing 20 has a housing opening 201. As shown in FIG. 2, FIG. 5 and FIG. 6, a first end 31 of the sleeve 30 is located inside the housing 20, and a second end 32 of the sleeve 30 has a sleeve opening 301 and extends out from the housing opening 201. A part of the sleeve is axially slidable inside the housing 20. As shown in FIG. 2, FIG. 7 and FIG. 8, a first end 41 of the core 40 is disposed in the housing 20, and is sleeved to the needle holder 10. A second end 42 of the core 40 has a core hole 401 through which an end 61 (as shown in FIG. 11) of the tube needle 60 extends. The spring 50 is adapted to provide an elastic force for moving the sleeve 30 axially toward the outside of the housing 20. The sleeve 30 is adapted to retract into the housing 20 by an external force, such that the tube needle 60 is exposed through the sleeve opening 301, as shown in FIG. 14. As shown in FIG. 7, FIG. 9 and FIG. 12, the first end 41 of the core 40 is provided with a core guiding portion 402 extending radially, and the needle holder 10 is provided with a guiding engagement portion. In the assembled position of the core 40 and the needle holder 10, the core guiding portion 402 engages with the guiding engagement portion, as shown in FIG. 12. As shown in FIGS. 13 to 16, the sleeve 30 moves toward the inside of the housing 20. In this way, the core guiding portion 402 moves along the guiding engagement portion, to guide the core 40 to rotate in a circumferential direction until the core guiding portion 402 moves to disengage from the guiding engagement portion.

In the embodiment of the present disclosure, the needle holder 10 of the disposable injection needle is sleeved with the core 40. The tube needle 60 extends axially through the core hole 401 of the core 40, and is exposed through the sleeve opening 301 of the sleeve 30. In an initial assembly state of the disposable injection needle, for example, as shown in FIG. 12, the first end 31 of the sleeve 30 is sleeved on the core 40 and located inside the housing 20. The first end 21 of the housing 20 is connected to the second end 12 of the needle holder 10, and the second end 22 of the housing 20 engages with the sleeve 30. In this state, the core guiding portion 402 of the core 40 engages with the guiding engagement portion of the needle holder 10. When the disposable injection needle is in use, an external force is applied to the disposable injection needle. The sleeve 30 moves toward the needle holder 10 under the external force, that is, retracts into the housing 20, which can generate a pushing force on the core 40. With this pushing force, the core 40 rotates circumferentially such that the core guiding portion 402 moves along the guiding engagement portion to guide the core 40 to rotate in the circumferential direction. The core guiding portion 402 continues to move until it disengages from the guiding engagement portion. In this way, the sleeve moves axially toward the outside of the housing 20 under an elastic force of the spring, thereby covering the tube needle to avoid increased chance of infection by secondary use.

Referring to FIG. 5, the sleeve 30 is provided with a small-diameter portion 302 and a large-diameter portion 303, which are connected to each other in an axial direction. The small-diameter portion and the large-diameter portion form a step surface 304 at the connection. The small-diameter portion 302 is adapted to extend out of the sleeve 30 through the housing opening 201, and a distal end of the small-diameter portion 302 has the sleeve opening 301. In addition, as shown in FIG. 3, the second end 22 of the housing 20 has a housing blocking surface 202 for defining the housing opening 201. The step surface 304 is adapted to abut against the housing blocking surface 202, as shown in FIGS. 2 and 12. The large-diameter portion 303 is axially slidable inside the housing 20.

As shown in FIG. 6, FIG. 7 and FIG. 15, in an embodiment, an inner wall of the sleeve 30 is provided with a blocking member 305 that extends in the axial direction. An outer wall of the core 40 is provided with a limit guiding groove 403 that extends in the axial direction, as shown in FIG. 18. The blocking member 305 moves in the limit guiding groove 403 by the rotation of the core 40 circumferentially, as shown in FIGS. 13 and 15. In an alternative embodiment, the inner wall of the sleeve 30 is provided with a plurality of blocking members 305, which are spaced apart from each other, as shown in FIG. 6. The outer wall of the core 40 is provided with a plurality of limit guiding grooves 403, which are spaced apart from each other. Each of the plurality of blocking members 305 moves in a corresponding one of the plurality of limit guiding grooves 403 by the circumferential rotation of the core 40.

In an embodiment of the present disclosure, as shown in FIG. 7, the limit guiding groove 403 includes a first guiding groove portion 4031 and a second guiding groove portion 4032, which are disposed in the axial direction. The circumferential dimension of the first guiding groove portion is greater than that of the second guiding groove portion. The circumferential rotation of the core 40 causes the blocking member 305 to rotate axially and circumferentially from the first guiding groove portion 4031 to the second guiding groove portion 4032, and the blocking member is stopped in the second guiding groove portion 4032, thereby preventing further rotation of the core, as shown in FIGS. 13 to 15. For example, the core rotates to a position where the side wall of the blocking member 305 engages with the side wall of the limit guiding groove 403, thereby preventing further rotation of the core.

In an embodiment, an end portion of the first guiding groove portion 4031 close to the second guiding groove portion 4032 has a guiding surface 4033, and an end portion of the blocking member 305 has an engagement surface that is adapted to engage with the guiding surface 4033.

As shown in FIG. 7, in the embodiment of the present disclosure, two side walls of the limit guiding groove 403 in the circumferential direction extend to a position close to the core hole 401 and form a sleeve blocking surface 404. When the external force applied to the sleeve is removed, the sleeve 30 moves toward the sleeve opening 301 under the elastic force of the spring 50, as shown in FIG. 16. In this way, after the injection needle of the present disclosure is used, the end portion of the blocking member 305 of the sleeve abuts against the sleeve blocking surface 404 of the core 40 if the sleeve is again pressed downwards. Accordingly, the sleeve cannot be pressed downwards and retract back into the housing 20 once again to expose the tube needle, thereby preventing the used needle from accidentally injuring others to cause cross infection.

As shown in FIG. 11, a bottom of the needle holder 10 may be provided with a partition plate 101, and the first end 11 and the second end 12 of the needle holder are located respectively on two sides of the partition plate. Refer to FIG. 9, the partition plate has a limit surface 1011, and the guiding engagement portion extends axially from the limit surface 1011 toward the housing opening 201 and is located at an edge of the limit surface 1011. After the circumferential rotation of the core 40 has been accomplished, the first end 21 of the core abuts against the limit surface 1011 to prevent further axial movement of the core. The needle holder 10 may include a core limit portion 102 connected with the guiding engagement portion, and the core limit portion is adapted to prevent the core 40 from further moving in the circumferential direction after accomplishing the circumferential rotation.

Further, as shown in FIG. 7, the first end 41 of the core 40 is provided with a boss portion 405 extending radially from the core. The core guiding portion 402 extends radially from an edge of the boss portion 405 toward the needle holder 10, as shown in FIG. 11. The guiding engagement portion is disposed on a radially outer side of the boss portion 405, as shown in FIG. 12. The boss portion 405 has a boss top surface 4051 and a boss bottom surface 4052. An end of the spring 50 abuts against the boss top surface 4051. After the circumferential rotation of the core 40 is accomplished, the boss bottom surface 4052 or the core guiding portion 402 abuts against the limit surface 1011.

In an embodiment shown in FIG. 9, the guiding engagement portion of the needle holder 10 includes a guiding flat surface 103 and a guiding slope 104, which obliquely extends from the guiding flat surface to the limit surface 1011. As shown in FIG. 12, the core guiding portion 402 engages with the guiding flat surface 103 at the installation position of the core 40 and the needle holder. The sleeve 30 moves toward the interior of the housing 20, such that the core guiding portion 402 rotates from the guiding flat surface 103 to the guiding slope 104 in the circumferential direction, to guide the core to rotate in the circumferential direction. The core guiding portion 402 is adapted to moves to disengage from the guiding slope 104.

In an embodiment, the needle holder 10 is provided with a plurality of guiding engagement portions 103, 104, and the core limit portion 102 is a core limit groove between two adjacent guiding engagement portions of the plurality of guiding engagement portions, as shown in FIG. 9.

As shown in FIG. 9, the needle holder 10 may further include a sleeve blocking portion 105, which is adjacent to the guiding engagement portion. The height of the sleeve blocking portion 105 in the axial direction is greater than that of the guiding engagement portion in the axial direction, and the sleeve blocking portion 105 is configured to prevent the sleeve 30 from moving toward the interior of the housing 20. In an embodiment, as shown in FIG. 9, the needle holder 10 is provided with a needle holder through hole 106 at the center thereof, and the tube needle 60 passes through the needle holder through hole.

Referring to FIG. 4, the first end 21 of the housing 20 is provided with a base 203, and a transverse groove 204 is formed circumferentially on an inner wall of the base and surrounds the inner wall of the base. As shown in FIG. 9, the second end 12 of the needle holder 10 is provided with a transverse rib 107, which surrounds the outer wall of the needle holder in the radial direction. When the disposable injection needle is assembled, the transverse rib 107 fits in the transverse groove 204 to allow the needle holder 10 to be fixed axially in position with respect to the housing 20.

Continuing to refer to FIG. 9, the second end 12 of the needle holder 10 may further include a needle holder clamping groove 108 extending in the axial direction, and the needle holder clamping groove is located on the outer wall of the needle holder. As shown in FIGS. 4 and 12, the inner wall of the base 203 of the housing 20 may be further provided with a convex rib 205 extending in the axial direction, and the convex rib is adapted to fit in the needle holder clamping groove 108, thereby preventing the needle holder 10 from rotating relative to the housing 20 in the circumferential direction.

In an embodiment of the present disclosure, as shown in FIG. 5, the first end 31 of the sleeve 30 may include a sleeve limit groove 306, and the sleeve limit groove is formed on the outer wall of the sleeve. The inner wall of the housing 20 is provided with a limit rib 206 extending in the axial direction, and the limit rib is adapted to fit in the sleeve limit groove, as shown in FIG. 10.

In an embodiment, as shown in FIG. 5, the sleeve limit groove 306 may include a first limit groove portion 3061 and a second limit groove portion 3062, which are arranged in the axial direction. The first limit groove portion has a triangular section, and the second limit groove portion has a rectangular section. In this embodiment, the width of the first limit groove portion is greater than that of the second limit groove portion such that the limit rib 206 can be inserted into the sleeve limit groove 306, and thus the assembly of the sleeve and the housing is easier. It should be noted that the structure and shape of the sleeve limit groove are merely exemplary, and are not intended to be limited thereto.

In an embodiment, as shown in FIGS. 1 and 2, the disposable injection needle may further include an outer cap 70, and the outer cap 70 sleeves outside the needle holder 10, the core 40, the housing 20, and the sleeve 30.

In an embodiment, a first anti-rotation structure, such as a rib, a protrusion, or an interference fit structure, is provided at the connection between the housing 20 and the needle holder 10, and a second anti-rotation structure, such as a rotation stop rib, a protrusion, or an interference fit structure, is provided at the connection between the outer cap 70 and the housing 20.

In an embodiment, as shown in FIGS. 1 and 2, the disposable injection needle may further include a sealing sticker 80, which covers an opening of the outer cap 70. Before the disposable injection needle can be used, it is required to tear off the sealing sticker 80 and take off the outer cap 70 to remove internal components, thereby further preventing failure of the injection needle due to mis-operation before the injection needle is used.

Hereinafter, an assembling process of an injection needle according to an embodiment of the present disclosure will be described with reference to the above structure.

The tube needle 60 passes through the needle holder through hole 106 of the needle holder 10. For example, the tube needle 60 may be fixed to the needle holder by an adhesive process. The needle holder 10 with the tube needle enters the core 40 from the bottom of the core 40, and the tube needle 60 passes through the core hole 401 of the core. The core guiding portion 402 of the core 40 is in contact with the guiding flat surface 103 of the needle holder 10.

Next, the spring 50 sleeves outside the core 40. An end of the spring 50 abuts against the boss portion 405 of the core 40, and another end of the spring is in contact with the blocking member 305 of the sleeve 30.

Thereafter, an assembly element of the above components is placed in the housing 20 from the bottom of the housing 20. The sleeve 30 protrudes from the housing opening 201, and the needle holder clamping groove 108 of the needle holder 10 engages with the convex rib 205 of the housing 20, such that the needle holder 10 and the housing 20 cannot rotate in the circumferential direction. The transverse convex rib 107 of the needle holder 10 is fitted in the transverse groove 204 of the housing 20 such that the needle holder 10 cannot move with respect to the housing 20 in the axial direction. The step surface 304 of the sleeve 30 is in contact with the housing blocking surface 202 of the housing 20 under the action of the spring 50 so as to be assembled to an initial state, as shown in FIG. 12.

An operation process of the disposable injection needle according to an embodiment of the present disclosure is described below with reference to the structure described above.

When the disposable injection needle is in use, the sleeve 30 moves toward the needle holder 10 under an external force, that is, moves toward the interior of the housing 20. When the blocking member 305 of the sleeve 30 is in contact with the guiding surface 4033 of the core 40, the blocking member 305 applies a pushing force to the guiding surface 4033. The core 40 rotates circumferentially under the pushing force, and the core guiding portion 402 of the core 40 and the guiding flat surface 103 of the needle holder 10 are gradually separated from each other, until the core guiding portion 402 is no longer in contact with the guiding flat surface 103, as shown in FIG. 13.

After the core guiding portion 402 of the core 40 is separated from the guiding flat surface 103 of the needle holder 10, the core 40 continues to move in the circumferential direction under the elastic force of the spring 50 and is in contact with the guiding slope 104 of the needle holder 10. In this way, the core 40 rotates in the circumferential direction while moving in the axial direction. In this process, the blocking member 305 of the sleeve moves in the limit guiding groove 403 of the core 40 until the core 40 rotates to a position where the side wall of the blocking member 305 engages with the side wall of the limit guiding groove 403, thereby preventing the core from further rotating, as shown in FIG. 14 and FIG. 15.

When the sleeve 30 moves toward the needle holder 10, the tube needle 60 is exposed through the sleeve opening 301 of the sleeve 30. When the sleeve 30 is pressed such that a bottom surface 307 of the sleeve is in contact with the sleeve blocking portion 105 of the needle holder 10 or the sleeve opening 301 is lower than the housing opening 201 of the housing 20, the tube needle 60 exposes longest, as shown in FIG. 14.

After the injection needle is used, the sleeve 30 is no longer subject to downward force. In this case, the sleeve 30 ejects upwards under the force of the spring. When the sleeve 30 moves to a position where the blocking member 305 thereof is separated from the limit guiding groove 403 of the core 40, the core guiding portion 402 of the core 40 slides along the guiding slope 104 of the needle holder 10 under the acting force of the spring 50, until the core guiding portion 402 or the bottom surface 307 is in contact with the limit surface 1011 of the needle holder 10. In this way, under the acting force of the spring 50, the sleeve 30 moves axially to the step surface 304 of the sleeve 30 to contact the housing blocking surface 202 of the housing 20, as shown in FIG. 16.

In this state, an upper plane 407 of the core 40 is lower than a cavity top surface 207 of the housing 20. When the sleeve 30 is a transparent member, the change of the position of the core before and after use can be visually observed.

When the sleeve 30 is pressed again and the end portion of the blocking member 305 of the sleeve 30 is in contact with the sleeve blocking surface 404 of the core 40, it cannot move downwardly again, as shown in FIG. 17 and FIG. 18. In this case, the tube needle 60 is lower than the sleeve opening 301 of the sleeve 30, and therefore cannot be exposed for reuse.

The foregoing descriptions are merely embodiments of the present disclosure, and are not intended to limit the present disclosure thereto. Those skilled in the art can understand that any modifications, equivalent replacements or improvements, made without departing from the spirit and principle of the present disclosure, shall fall within the scope of the present disclosure.

What is claimed is:

1. A disposable injection needle, comprising:

a needle holder having a first end and a second end, a tube needle being provided to the needle holder and passing through the needle holder;

a housing having a first end and a second end, the first end of the housing being connected to the second end of the needle holder, and the second end of the housing having a housing opening;

a sleeve having a first end and a second end, the first end of the sleeve being located in the housing, the second end of the sleeve having a sleeve opening and protruding from the housing opening, and a part of the sleeve being axially slidable inside the housing;

a core having a first end and a second end, the first end of the core being disposed in the housing and being sleeved outside the needle holder, and the second end of the core comprising a core hole through which an end of the tube needle extends; and a spring configured to provide an elastic force to axially move the sleeve toward outside of the housing, wherein a first end of the spring is sleeved outside the core and seated against the core, and a second end of the spring is in contact with the sleeve and seated against the sleeve;

wherein the first end of the sleeve is sleeved outside the core, and the sleeve is configured to retract into the housing under an external force, to expose the tube needle through the sleeve opening;

wherein the first end of the core is provided with at least one core guiding portion extending radially outward, the needle holder is provided with at least one guiding engagement portion, and the at least one core guiding portion engages with the at least one guiding engagement portion correspondingly at an assembled position of the core and the needle holder; and wherein the at least one core guiding portion is configured to move along the at least one guiding engagement portion with movement of the sleeve toward an interior of the housing, to guide the core to rotate in a circumferential direction of the disposable injection needle, and as the spring pushes the sleeve toward outside of the housing, the core further rotates in the circumferential direction.

2. The disposable injection needle according to claim 1, wherein the sleeve comprises a small-diameter portion and a large-diameter portion that are connected to each other in an axial direction of the disposable injection needle, the small-diameter portion and the large-diameter portion form a step surface at connection thereof, the small-diameter portion is configured to protrude outside the sleeve through the housing opening, and the small-diameter portion has a distal end at which the sleeve opening is formed;

the second end of the housing has a housing blocking surface configured to define the housing opening; and the step surface is configured to abut against the housing blocking surface, and the large-diameter portion is axially slidable inside the housing.

3. The disposable injection needle according to claim 2, wherein an inner wall of the sleeve is provided with at least one blocking member extending in the axial direction;

an outer wall of the core is provided with at least one limit guiding groove extending in the axial direction; and the at least one blocking member is configured to move inside the at least one limit guiding groove correspondingly with the rotation of the core in the circumferential direction.

4. The disposable injection needle according to claim 3, wherein one of the at least one limit guiding groove comprises a first guiding groove portion and a second guiding groove portion that are disposed in the axial direction, and a dimension of the first guiding groove portion in the circumferential direction is greater than a dimension of the second guiding groove portion in the circumferential direction; and based on the rotation of the core in the circumferential direction, one of the at least one blocking member is configured to move axially and rotate circumferentially from the first guiding groove portion to the second guiding groove portion, and is stopped in the second guiding groove portion.

5. The disposable injection needle according to claim 4, wherein an end portion of the first guiding groove portion close to the second guiding groove portion has a guiding surface; and an end portion of the one of the at least one blocking member has an engagement surface that is configured to engage with the guiding surface.

6. The disposable injection needle according to claim 3, wherein the at least one blocking member comprises a plurality of blocking members that are spaced apart from each other, the at least one limit guiding groove comprises a plurality of limit guiding grooves that are spaced apart from each other; and each of the plurality of blocking members is configured to move in a corresponding one of the plurality of limit guiding grooves with the rotation of the core in the circumferential direction.

7. The disposable injection needle according to claim 3, wherein two sidewalls of one of the at least one limit guiding groove are spaced apart circumferentially and extend to a position close to the core hole, and each form a sleeve blocking surface.

8. The disposable injection needle according to claim 1, wherein the needle holder is provided with a partition plate, and the first end and the second end of the needle holder are located respectively on two opposite sides of the partition plate;

the partition plate has a limit plane, the at least one guiding engagement portion extends from the limit plane toward the housing opening in an axial direction of the disposable injection needle, and the at least one guiding engagement portion is located at an edge of the limit plane;

after the rotation of the core in the circumferential direction is accomplished, the first end of the core abuts against the limit plane to prevent further axial movement of the core; and the needle holder is further provided with a core limit portion, the core limit portion is disposed adjacent to one of the at least one guiding engagement portion, and the core limit portion is configured to prevent the core from further moving in the circumferential direction after the circumferential rotation.

9. The disposable injection needle according to claim 8, wherein the first end of the core is provided with a boss portion extending radially from the core, the at least one core guiding portion extends radially from an edge of the boss portion toward the needle holder, and the at least one guiding engagement portion is disposed on a radially outer side of the boss portion;

the boss portion has a boss top surface and a boss bottom surface, and the first end of the spring abuts against the boss top surface; and the boss bottom surface of the come guiding portion abuts against the limit plane after finishing the rotation of the core in the circumferential direction.

10. The disposable injection needle according to claim 9, wherein one of the at least one guiding engagement portion comprises a guiding flat surface and a guiding slope, and the guiding slope obliquely extends from the guiding flat surface to the limit plane;

on the assembled position of the core and the needle holder, one of the at least one core guiding portion engages with the guiding flat surface; and the one of the at least one core guiding portion is configured to rotate from the guiding flat surface to the guiding slope in the circumferential direction with the movement of the sleeve toward the interior of the housing, to guide the core to rotate in the circumferential direction, and the one of the at least one core guiding portion is configured to move to disengage from the guiding slope.

11. The disposable injection needle according to claim 8, wherein the at least one guiding engagement portion comprises a plurality of guiding engagement portions, and the core limit portion is a core limit groove between two adjacent ones of the plurality of guiding engagement portions.

12. The disposable injection needle according to claim 8, wherein the needle holder further comprises:

a sleeve blocking portion disposed adjacent to the at least one guiding engagement portion, a height of the sleeve blocking portion in the axial direction being greater than a height of the at least one guiding engagement portion in the axial direction, and the sleeve blocking portion being configured to prevent the sleeve from moving toward the interior of the housing.

13. The disposable injection needle according to claim 8, wherein the needle holder has a needle holder through-hole at a center thereof, and the tube needle passes through the needle holder through-hole.

14. The disposable injection needle according to claim 1, wherein the first end of the housing comprises a base, and an inner wall of the base is provided with a transverse groove that is formed circumferentially around the inner wall;

the second end of the needle holder is provided with a transverse rib, and the transverse rib is disposed radially around an outer wall of the needle holder; and the transverse rib is configured to be fitted in the transverse groove.

15. The disposable injection needle according to claim 14, wherein the second end of the needle holder is further provided with a needle holder clamping groove extending in an axial direction of the disposable injection needle, and the needle holder clamping groove is located on the outer wall of the needle holder; and the inner wall of the base is further provided with a convex rib extending in the axial direction, and the convex rib is configured to be fitted in the needle holder clamping groove.

16. The disposable injection needle according to claim 1, wherein the first end of the sleeve is provided with a sleeve limit groove, and the sleeve limit groove is formed on an outer wall of the sleeve; and the housing is provided with a limit rib extending in an axial direction of the disposable injection needle on an inner wall thereof, and the limit rib is configured to be fitted in the sleeve limit groove.

17. The disposable injection needle according to claim 16, wherein the sleeve limit groove comprises a first limit groove portion and a second limit groove portion that are arranged in the axial direction, the first limit groove portion has a triangular section, and the second limit groove portion has a rectangular section.

18. The disposable injection needle according to claim 1, further comprising:

an outer cap, the outer cap being sleeved outside the needle holder, the core, the housing, and the sleeve.

19. The disposable injection needle according to claim 18, further comprising:

a first anti-rotation structure provided at a connection between the housing and the needle holder; and a second anti-rotation structure provided at a connection between the outer cap and the housing.

20. The disposable injection needle according to claim 18, further comprising:

a sealing sticker covering an opening of the outer cap.

* * * * *